United States Patent
Van Der Brug

[19]

[11] Patent Number: 5,817,105
[45] Date of Patent: Oct. 6, 1998

[54] IMAGE-GUIDED SURGERY SYSTEM

[75] Inventor: Willem P. Van Der Brug, Eindhoven, Netherlands

[73] Assignee: U.S. Philips Corporation, New York, N.Y.

[21] Appl. No.: 855,042

[22] Filed: May 13, 1997

[30] Foreign Application Priority Data

May 29, 1996 [EP] European Pat. Off. ........... 96201485.8

[51] Int. Cl.$^6$ .................................................. A61B 19/00
[52] U.S. Cl. .......................................... 606/130; 600/426
[58] Field of Search ..................... 606/130; 128/653.1, 128/653.2; 600/424, 425, 426, 429

[56] References Cited

U.S. PATENT DOCUMENTS

| | | | |
|---|---|---|---|
| 5,078,140 | 1/1992 | Kwoh | 606/130 X |
| 5,097,839 | 3/1992 | Allen | 606/130 X |
| 5,119,817 | 6/1992 | Allen | 606/130 X |
| 5,160,337 | 11/1992 | Cosman | 606/130 |
| 5,186,174 | 2/1993 | Schlondorff et al. | 606/130 X |
| 5,251,127 | 10/1993 | Raab | 606/130 X |
| 5,389,101 | 2/1995 | Heilbrun et al. | 606/130 |
| 5,662,111 | 9/1997 | Cosman | 606/130 X |

*Primary Examiner*—Wynn Wood Coggins
*Assistant Examiner*—A. T. Nguyen
*Attorney, Agent, or Firm*—Jack D. Slobod; Dwight H. Renfrew

[57] ABSTRACT

An image-guided surgery system includes an optical position measuring system (1, 2) for measuring the position of a surgical instrument (13) relative to a patient (14) to be operated or treated. Using a data processor (2), the position of the surgical instrument (13) is reproduced in an image displayed on a monitor (16). The optical position measuring system (1, 2) includes a camera unit (1) with two cameras (10). The camera unit (1) also includes a memory unit (3) in which data concerning the positions of the cameras (10) in the camera unit (1) relative to one another are stored.

6 Claims, 2 Drawing Sheets

IMAGE-GUIDED SURGERY SYSTEM

BACKGROUND OF THE INVENTION

1. Field of the Invention

The invention relates to an image-guided surgery system, including an optical position measuring system for measuring the position of a surgical instrument relative to a patient, which optical position measuring system includes a camera unit with two or more cameras, and a calibration memory for storing the positions of the cameras in the camera unit relative to one another.

2. Description of the Related Art

An image-guided surgery system of this kind is known from U.S. Pat. No. 5,389,101.

An image-guided surgery system is used to show a surgeon the position of a surgical instrument in an operating zone in the body of the patient during surgery. Prior to surgery, images (for example, CT or MRI images) are made of the patient. During surgery the position measuring system measures the position of the surgical instrument relative to the patient and a data processor calculates the position in such a prerecorded image which corresponds to the measured position of the surgical instrument. The prerecorded image is displayed on a monitor and the actual position of the surgical instrument is indicated therein. The surgeon can see where the surgical instrument is situated in the operating zone by observing the image displayed on the monitor, without the surgeon having a direct view thereof. The image on the monitor reveals how the surgeon can move the surgical instrument in the operating zone without serious risk of unnecessarily damaging tissues and notably without risk of damaging vital organs.

An image-guided surgery system of this kind is preferably used in neurosurgery for showing the surgeon exactly where in the brain the surgical instrument is situated during cerebral surgery.

The position measuring system measures the position of the surgical instrument by recording images of the surgical instrument from different directions by means of two cameras. The data processor derives the position of the surgical instrument relative to the patient during surgery from image signals from the individual cameras and from the positions of the cameras relative to one another. The data processor of the known image-guided surgery system includes a calibration memory in which data concerning the positions of the cameras relative to one another is stored. The data processor fetches the positions of the cameras relative to one another, required for the calculation of the position of the surgical instrument, from the calibration memory. It is a drawback of the known image-guided surgery system that a substantial amount of time is lost when the camera unit is to be replaced.

It is an object of the invention to provide an image-guided surgery system whose camera unit can be replaced quickly and simply.

This object is achieved by means of an image-guided surgery system according to the invention which is characterized in that the calibration memory is accommodated in the camera unit.

DETAILED DESCRIPTION OF THE PREFERRED EMBODIMENTS

The calibration memory is loaded with the position data representing the positions of the cameras relative to one another. The position data is measured after the cameras have been mounted in the camera unit. When a camera unit is replaced, for example because of a defect in one of the cameras, the position data relating to the substitute camera unit are immediately available. This is because the substitute camera unit also includes a calibration memory loaded with the relevant position data. When the camera unit of an image-guided surgery system according to the invention is replaced, it is not necessary to measure the positions of the cameras relative to one another again and to reload the calibration memory. It is thus achieved that the image-guided surgery system is ready again for use practically immediately after replacement of the camera unit.

It is also possible for separate image-guided surgery systems to share camera units, i.e. various camera units are available as common units for separate image-guided surgery systems. The individual camera units can be used at will for individual image-guided surgery systems, without the interchanging introducing a risk of errors in the measured position of the surgical instrument.

A preferred embodiment of an image-guided surgery system according to the invention is characterized in that the calibration memory is provided with a Flash-EPROM.

A Flash-EPROM offers the advantage that it is particularly reliable. Moreover, contemporary Flash-EPROMs are comparatively inexpensive.

A further preferred embodiment of an image-guided surgery system according to the invention is characterized in that the camera unit includes a microcontroller. The calibration memory and the microcontroller are preferably combined in an integrated circuit.

The main task of the microcontroller is to provide the communication between the data processor and the calibration memory. For the calibration memory preferably a Flash-EPROM is used, because the latter can be integrated with the microcontroller in one integrated circuit.

BRIEF DESCRIPTION OF THE DRAWING

These and other aspects of the invention will be apparent from and elucidated with reference to the embodiment described hereinafter. In the drawings:

FIG. 1 shows diagrammatically an image-guided surgery system in which the invention is used. The image-guided surgery system includes the data processor 2 and the camera unit 1 with two cameras 10. The data processor 2 includes a computer 31. The optical position measuring system includes the camera unit 1 and the computer 31 included in the data processor 2. The cameras pick up infrared signals which are emitted by three or more infrared sources 11, for example infrared emitting diodes (IREDs) mounted on the handle 12 of a surgical instrument 13. On the basis of the images of the IREDs 11 as picked up by the individual cameras 10, the computer 31 determines the position of the surgical instrument 13 in the operating zone relative to the patient 14 undergoing surgery. The positions of the cameras 10 relative to one another are also required in order to calculate the position of the surgical instrument. These positions are represented by position data stored in the calibration memory 3. The computer 31 derives the necessary position data from the calibration memory 3. The surgical instrument 13 is handled by a surgeon 15. Image information of the operating zone of the patient 14 is displayed on the monitor 16. The image information is, for example CT data or MRI data which has been recorded prior to the surgery so as to be stored in a memory unit 33 of the data processor 2. If desired, image information can be acquired again during surgery; for example, new CT images or MRI images can be picked up if necessary. The position of the surgical instrument 13 as calculated by the computer 31 is transformed into the corresponding position in the CT image and/or MRI image. The transformed position and the CT data and/or MRI data are applied to an image processing unit 32 of the data processor 2 which derives an image signal therefrom which represents the image information of the CT data and/or MRI data, together with the position of the surgical instrument 13. The image displayed on the monitor 16 also shows the position of the surgical instrument in the operating zone. The surgeon 15 is thus assisted in making the surgical instrument reach a desired location in the operating zone. It is not necessary now to form X-ray images continuously and it is not necessary either to remove large amounts of tissue so as to reach the desired location or to gain a more direct view of the surgical instrument in the operating zone. The image-guided surgery system allows for locations to be reached which are otherwise difficult to operate without unjustified risks for the patient.

In order to relate positions, notably the coordinates thereof, in the operating zone to positions in the image displayed, it is necessary to calibrate the image-guided surgery system. Given marks are included in the image information. These marks are, for example X-ray absorbing small objects or small objects which can be perceived by means of magnetic resonance. During calibration of the image-guided surgery system, the marks on the patient to be operated are successively pointed at by means of the surgical instrument and the positions of the marks on the patient are measured by means of the optical position measuring system. The computer 31 then calculates the transformation between the positions of the marks on the patient and the corresponding positions of the reproduction of the marks in the image displayed. This transformation also describes the relations between positions in the operating zone and positions in the reproduction of the image information of the relevant operating zone.

Figure 1:
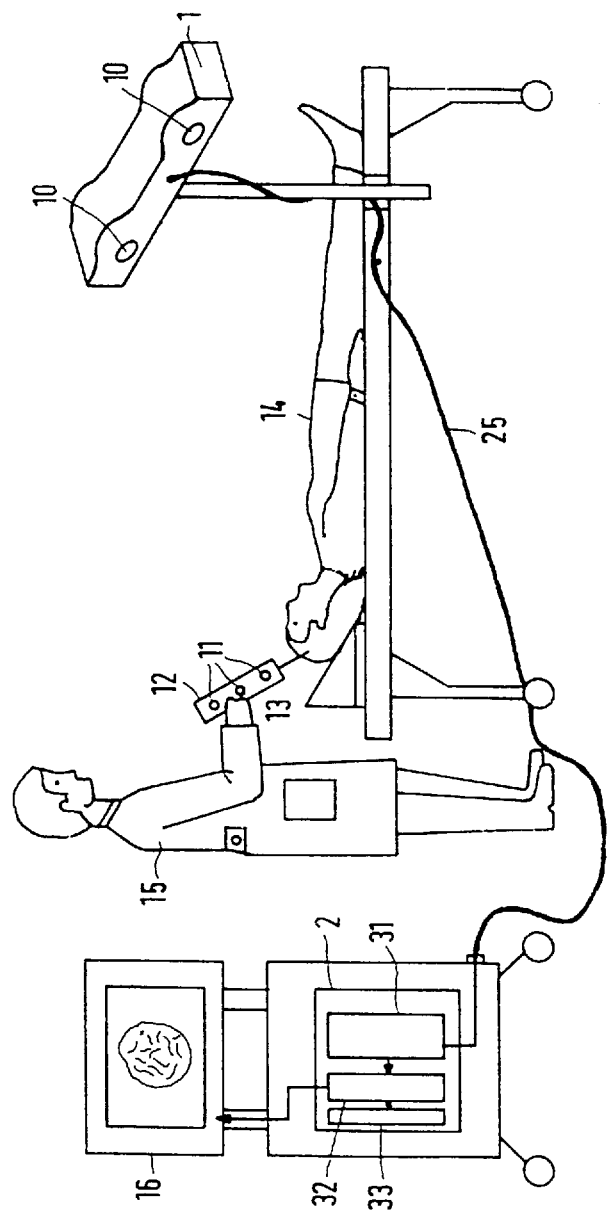
FIG. 1 shows diagrammatically an image-guided surgery system in which the invention is used.
Figure 2:
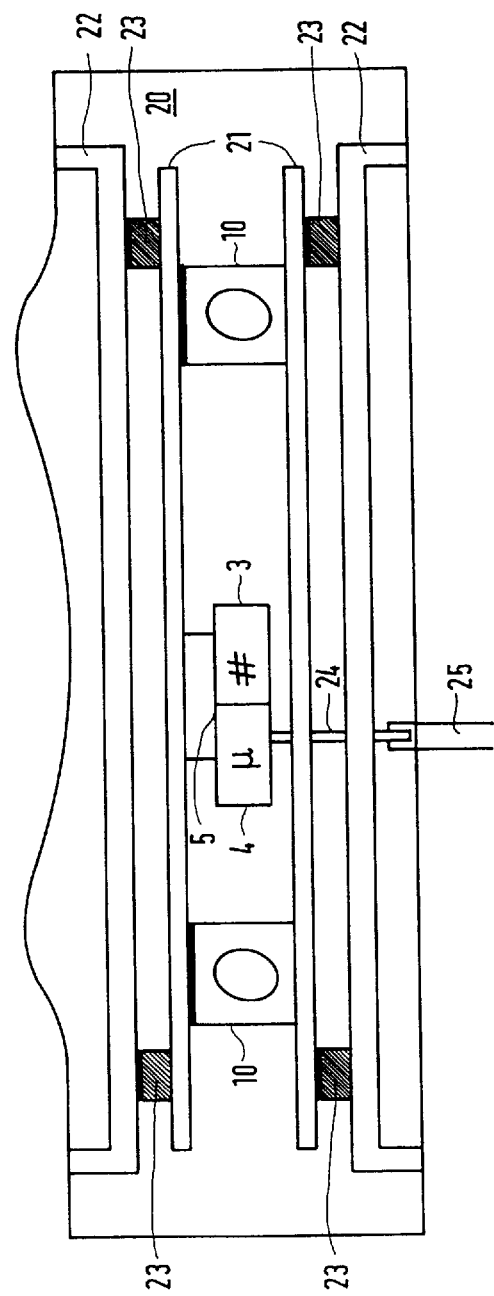
FIG. 2 shows diagrammatically the camera unit of the image-guided surgery system shown in FIG. 1.

FIG. 2 shows diagrammatically the camera unit of the image-guided surgery system shown in FIG. 1.

The cameras 10 are mounted in a camera frame 20 in order to ensure that the distance between the cameras is not excessively susceptible to temperature fluctuations and/or shocks. The camera frame 20 includes a lightweight support 21 which is made of a titanium alloy and is suspended from an aluminium chassis 22. The support 21 is suspended from the chassis 22 by means of resilient means 23, for example shock absorbers.

After mounting of the cameras in the camera unit, the positions of the cameras relative to one another are accurately measured. These positions are stored in the calibration memory 3 as a calibration data set. The calibration set is read by the microcontroller 4 and applied to the data processor 2 via a cable connection. To this end an output 24 of the microcontroller 4 is connected to the cable 25. Preferably, the calibration memory 3 is a Flash-EPROM which can be integrated in an integrated circuit 5 together with the microcontroller 4.

I claim:

1. An image-guided surgery system, comprising an optical position measuring system for measuring the position of a surgical instrument relative to a patient, which optical position measuring system includes a camera unit with two or more cameras, and a calibration memory means for storing the positions of the cameras in the camera unit relative to one another, which calibration memory means is accommodated in the camera unit.

2. An image-guided surgery system as claimed in claim 1, wherein the calibration memory means is provided with a Flash-EPROM.

3. An image-guided surgery system as claimed in claim 1, wherein the camera unit includes a microcontroller.

4. An image-guided surgery system as claimed in claim 3, wherein the calibration memory means and the microcontroller are integrated in one integrated circuit.

5. An image-guided surgery system as claimed in claim 2, wherein the camera unit includes a microcontroller.

6. An image-guided surgery system as claimed in claim 5, wherein the calibration memory means and the microcontroller are integrated in one integrated circuit.

* * * * *